Figure 1:
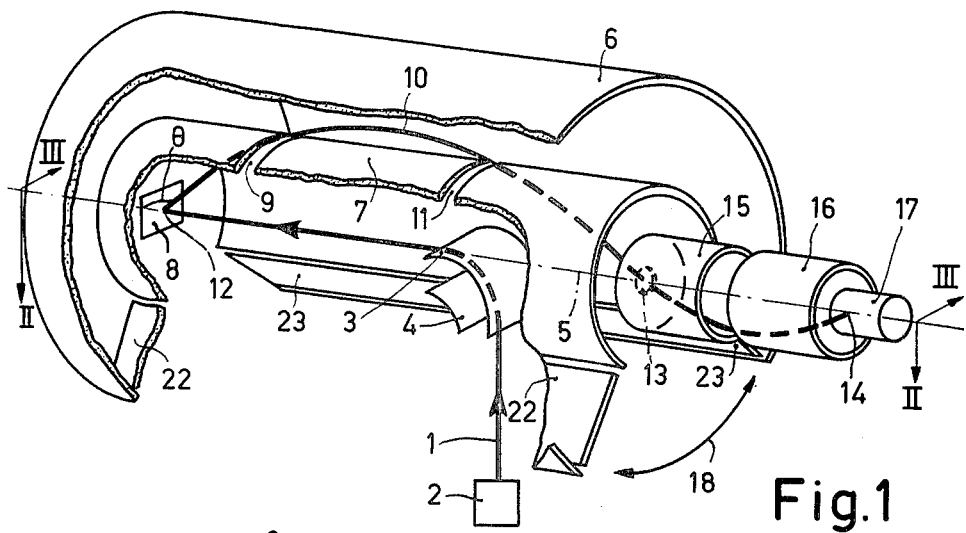

United States Patent [19]

Brongersma

[11] 4,100,409
[45] Jul. 11, 1978

[54] DEVICE FOR ANALYZING A SURFACE LAYER BY MEANS OF ION SCATTERING

[75] Inventor: Hidde Herman Brongersma, Eindhoven, Netherlands

[73] Assignee: U.S. Phillips Corporation, New York, N.Y.

[21] Appl. No.: 737,733

[22] Filed: Nov. 1, 1976

Related U.S. Application Data

[63] Continuation of Ser. No. 577,069, May 13, 1975, abandoned, which is a continuation of Ser. No. 432,483, Jan. 11, 1974, abandoned.

[30] Foreign Application Priority Data

Feb. 3, 1973 [NL] Netherlands .......................... 7301496

[51] Int. Cl.² ............................................. H01J 39/00
[52] U.S. Cl. ........................ 250/305; 250/310
[58] Field of Search .............. 250/305, 306, 309, 310, 250/398

[56] References Cited

U.S. PATENT DOCUMENTS

| 3,445,708 | 5/1969 | Webster | 250/305 |
|---|---|---|---|
| 3,517,191 | 6/1970 | Liebl | 250/309 |
| 3,609,352 | 9/1971 | Harris | 250/305 |
| 3,739,170 | 6/1973 | Bohen et al. | 250/305 |
| 3,783,280 | 1/1974 | Watson | 250/305 |
| 3,805,057 | 4/1974 | Yanagisawa | 250/305 |

Primary Examiner—Davis L. Willis
Assistant Examiner—B. Anderson
Attorney, Agent, or Firm—Frank R. Trifari

[57] ABSTRACT

A device for analysing a surface layer by means of ion scattering. The device comprises an energy selector having two coaxial cylindrical electrodes. A primary mono-energetic ion beam impinges upon the surface layer and its axis coincides with the axis of the cylindrical electrodes. Back-scattered ions, the paths of which lie on a conical surface having an apical angle of 180° reduced with the scattering angle, are selected for energy and detected.

2 Claims, 3 Drawing Figures

DEVICE FOR ANALYZING A SURFACE LAYER BY MEANS OF ION SCATTERING

This is a continuation of Ser. No. 577,069, filed May 13, 1975, now abandoned which was a continuation of Ser. No. 432,483, filed Jan. 11, 1974, now abandoned.

The invention relates to a device for analyzing a surface layer by means of ion scattering comprising: means to produce a primary, substantially mono-energetic ion beam, deflection means to direct the primary ion beam onto said surface layer, a diaphragm aperture to pass ions which are scattered at a predetermined angle relative to the axis of the primary ion beam at said surface layer, and an electrostatic analyzer and a detector to determine the kinetic enegy of the scattered ions passed through said diaphragm.

Such a device is known from the U.S. Pat. No. 3,480,774. In such an ion scattering spectrometer the surface layer to be investigated is bombarded with a primary ion beam. The ions of said beam collide with the atoms of the surface layer, which collisions may be assumed to be elastic in certain conditions. This means that the kinetic energy of an ion after the collision can be calculated by means of the principle of conversation of energy and momentum. If $E_1$ = kinetic energy of an ion before collision
$E_2$ = kinetic energy of an ion after collision
$m_1$ = mass of the ion
$m_2$ = mass of the atom in the surface layer against which the ion collides
$\gamma = m_2/m_1$
$\theta$ = the angle of scattering, that is the angle between the velocity vectors of the ion before and after collision, then it holds, if $\gamma > 1$, as is known that:

$$E_2 = \{[\cos\theta + (\gamma^2 - \sin^2\theta)^{\frac{1}{2}}]/(1 + \gamma)\}^2 E_1$$

From this it follows that $m_2$ can be determined by measuring $E_2$ if $m_1$, $E_1$ and $\theta$ are known and if it may be assumed that only single collisions take place. In an ion scattering spectrometer this is done as follows: A beam of ions, usually rare gas ions, of known mass $m_1$ and known energy $E_1$ is shot on the surface layer to be examined. A diaphragm is arranged so that the direction of scattered ions which pass through the gap enclose a known angle $\theta$ with the direction of the primary beam. The energy of the passed ions is measured in an energy analyzer. With a given voltage on the electrodes of the energy analyzer, only scattered ions of a given energy $E_2$ can pass through the analyzer. Hence said energy, given $m_1$, $E_1$ and $\theta$, is characteristic of the mass $m_2$ of atoms in the surface layer which are hit by the primary beam. By varying the voltage on the electrodes of the analyzer, a spectrum can be obtained of the types of atoms occurring in the surface layer. With given voltages on the analyzer, a peak occurs in the signal which the detector supplies. The value of the peak is a measure of the relative quantity of the relevant atoms and the voltage at the analyser associated with the peak is a measure of the mass of the relevant atoms.

It is obvious that the angle $\theta$ should be accurately determined and the aperture in the diagram should therefore be so small that only few scattered ions are passed. In practice, $\theta$ should be determined by the diaphragm to an accuracy of 1° to 2°, which results for the known device in that only scattered ions within a solid angle of 2° × 2° can be accepted so that only a very small signal is the result.

From the article "Zur Energieverteilung der von Protonen in Gasen ausgelöten Sekundärelectronen" in "Zeitschrift für Physik", Vol. 147 pp. 228-240, 1957 an energy analyzer is known which has two coaxial cylindrical electrodes. The advantage of such an analyzer is that the paths of the scattered ions which enclose a given angle with the axis of the analyzer, with which axis the axis of the primary beam coincides, lie on a conical surface. By using an annular diaphragm having a gap which is 2° wide and has a circumference of 360°, 180 times as many ions are accepted by the analyzer as by the analyzer which is used in the device described in the U.S. Pat. No. 3,480,774. However, such an analyzer could not be used so far in an ion scattering spectrometer because the primary ion beam must extend along axis of the analyzer and hence either the surface layer to be examined or the detector forms an obstruction to the primary ion beam.

It is the object of the invention to provide an ion scattering spectrometer in which an energy analyzer having two coaxial cylindrical electrodes can be used. Another object of the invention is to provide an ion scattering spectrometer which yields a considerably improved mass separation between the atoms present in the surface layer and which produces a considerably larger signal.

According to the invention, the device of the type stated in the first paragraph is characterized in that the electrostatic analyzer comprises two substantially cylindrical hollow coaxial electrodes, that the axis of the primary ion beam in a region adjoining the surface layer coincides with the axis of the analyzer, that the diaphragm aperture is substantially annular and coaxial with the analyzer and has a position to pass ions which are scattered over an angle exceeding 90°, that the coaxial electrodes are each provided with an aperture for passing the primary ion beam, and that the deflection means deflect the primary ion beam which enters through the apertures in the coaxial electrodes, along the axis of the analyzer.

Figure 2:
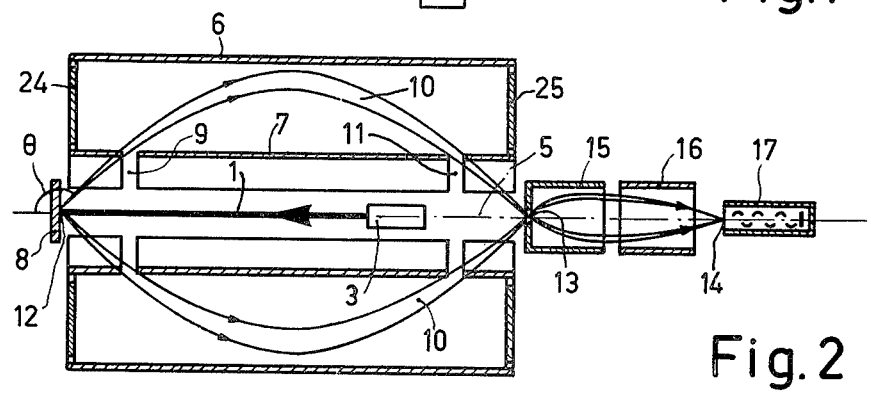
Figure 3:
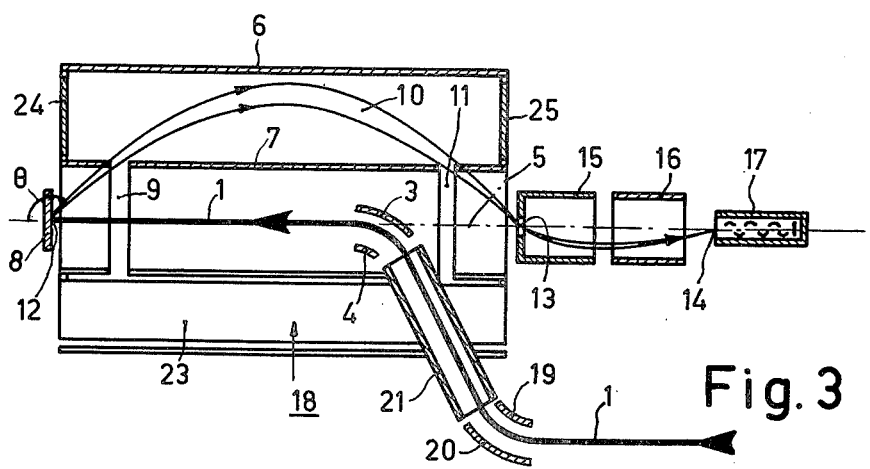

The invention will be described in greater detail with reference to the accompanying drawing, of which FIG. 1 is a perspective drawing of a device according to the invention partly broken away FIG. 2 is a cross-sectional view of said device of which the plane is perpendicular to the plane in which the primary beam enters, and FIG. 3 is a cross-sectional view of the said device, the plane of which coincides with the plane in which the primary beam enters.

In FIG. 1, a primary substantially monoenergetic ion beam 1 is produced by means 2 which are shown schematically and which comprise inter alia an ion source and means to direct the beam and to give it an given energy of, for example, a few hundred eV. Furthermore, the ions should be selected for mass and charge. Such means are well known in the art and need not be further explained. Rare gas ions, for example helium ions or neon ions, are preferably used. An advantage of these ions is their large ionization energy. This provides a fair chance that their charge is neutralized during the collision which, it is true, causes a small number of scattered ions, but also minimizes the possibility of multiple collisions which spoil the measurement. A device according to the invention has the property that also in the case of a small number of scattered ion, a still sufficient signal is produced by a detector.

The ion beam 1 is deflected by electrostatic deflection plates 3 and 4 until it extends along the axis 5 of the energy analyzer. The energy analyzer comprises two coaxial cylindrcal electrodes 6 and 7. A sector 18 of the cylindrical electrodes 6 and 7 which is as narrow as possible is open and forms an aperture to pass the entering beam. The ion beam 1 then impinges upon a target 8 which is arranged substantially perpendicular to the axis 5, in the point 12. The ions of the beam 1 collide against atoms in the surface layer of the target 8 and are scattered. They lose a given quantity of energy which depends upon the angle of scattering. The energy analyzer measures this energy loss for a given angle $\theta$ which is larger than 90°. So back-scattering is under consideration. The angle $\theta$ may be, for example, 138° so that the ions accepted by the energy analyzer describe paths over the surface of a cone having an optical angle of 84°. The angle $\theta$ is determined by the position of the diaphragm aperture 9 in the cylindrical electrode 7. The beam of scattered ions 10 in the radialelectric field between the electrodes 6 and 7 describes a quasi-parabolic path and can pass through the second diaphragm aperture 11 only with a given potential difference between the electrodes 6 and 7 which is a measure of the energy of the beam 10. Such an energy analyzer can focus the ion paths which start in the point 12 on the axis 5 in the point 13 on the axis 5. The focusing point 13 is reproduced in the point 14 which forms the input of a detector 17 by means of an electrostatic lens comprising the cylindrical electrodes 15 and 16. The detector 17 consists of an electron multiplier, the first dynode of which is hit by the ions to be detected.

For further illustration, FIGS. 2 and 3 show two cross-sectional views of the device, namely along the horizontal and vertical planes, respectively, of FIG. 1. FIG. 3 still shows a few details regarding the injection of the primary beam 1 which is carried out by means of a second set of electrostatic deflection plates 19 and 20 and an internally field-free tube 21.

For a good operation of the energy analyzer the electric field between the electrodes 6 and 7 should be equal everywhere to the field between two infinitely long axial cylinders. Since in practice the cylinders have a restricted length and moreover a sector 18 has been removed from the cylinders, electrodes must be provided to fix the peripheral conditions for the field and possibly to correct the field somewhat. The sector 18 is terminated by means of the plates 22 and 23. Perpendicular to the axis 5, the cylinders 6 and 7 are terminated by means of the plates 24 and 25 which are not shown in FIG. 1 for clarity. The plates 22, 23, 24 and 25 convey an average potential between that of the cylinders 6 and 7. It is also possible to divide the plates 22, 23, 24 and 25 into several electrodes having different potentials so as to obtain a better approach of the required electric field. The plates may also be manufactured from a material having a large electric resistance and be connected to the cylinders 6 and 7 so as to obtain a uniformly varying potential.

As already noted, a device according to the invention operates with back-scattering. Although fewer ions are scattered in the backward direction than in the forward direction, the device according to the invention is very suitable to detect small quantities of ions. The back-scattering described on the contrary has important advantages. First of all, with an angle of incidence of 90°, the possibility of sputtering is much smaller as a result of which the surface layer of the sample is less damaged by the primary beam. With an angle of incidence of 90° sputtering often does not occur until at 60 eV, while with an angle of 45° 10 eV is already sufficient. Secondly, the possibility of multiple collisions which spoil the measured result is much smaller with an angle of incidence of 90° than with angles smaller than 90°.

In the derivation of the collision formula used, the movement of the atoms of the target is neglected. This movement provides a windening of the peak in the signal of the detector. Cooling of the target may thus be of advantage so as to be able to distinguish between peaks of the spectrum which are located immediately beside each other.

The energy resolving power of the device can be increased by delaying the beam after a first energy analyzer and focusing it in such manner that a beam is formed having a divergence, in which the energy can be determined accurately by means of s second energy analyzer. The divergence desired for that purpose is approximately 42°. At low energy, such an energy analyzer can as a matter of fact detect smaller energy differences because $\Delta E/E$ (E is energy) for such an energy selector has a fixed value.

An advantage of the deflection of the primary beam with the deflection plates 3 and 4 and 19 and 20 is that differential pumping can be carried out better because there is no longer direct vision between the analyzer with target and the ion source. It should be noted that often a very low pressure of approximately $10^{-10}$ mm Hg is necessary at the target while the ion source operates at a pressure of approximately $10^{-1}$ mm Hg.

Near the target a low energy electron gun or a filament may be used so as to ensure in known manner space charge compensation. Furthermore it is possible to slowly peel the target layer by layer with a separate ion beam to be thus able to also analyze deeper located layers.

In the device shown in the drawing, the inner diameter of the electrode 6 is 130 mm and the outer diameter of the electrode 7 is 35 mm. The distance between the points 12 and 13 is 108.5 mm and the angle $\theta$ is 42.3°. The electrode 7 is earthed in connection with the transport of the primary beam 1. For selecting ions having an energy of V electron volts, the potential of the electrode 6 (relative to the electrode 7) must then be V volt.

What is claimed is:

1. In a cylindrical analyzer for charged particles back scattered from a target on the axis of said analyzer, said analyzer including inner and outer concentric electrically conductive tubular electrodes, the inner of said electrodes having longitudinally spaced annular entrance and exit slots for back scattered charged particles, a radial-electric field between said electrodes permitting back scattered charged particles having only a predetermined energy to exit through said exit slot to detector means therefor, the improvement comprising a passageway from the exterior of said analyzer to the interior thereof for cooperation with a primary monoenergetic ion beam source external thereto and deflection means within said analyzer to direct a primary mono-energetic ion beam through said passageway and along the axis of said analyzer for collision with the target on the axis thereof, said passageway comprising: at least two conductive radially aligned longitudinal walls between but spaced from said inner and outer electrodes and defining an acute sector shaped space therebetween, said inner and outer electrodes being absent from at least a portion of the boundary of said sector shaped space to form a passageway from the exterior of said analyzer to the interior thereof, said longitudinal walls being held at a potential between the potentials of said inner and outer electrodes.

2. The improvement of claim 1 wherein the charged particles are electrons.

* * * * *